United States Patent
Bretthauer et al.

(10) Patent No.: US 8,043,370 B2
(45) Date of Patent: Oct. 25, 2011

(54) OPTICAL DEVICE FOR RESTORING ACCOMMODATIVE CAPACITY OF THE EYE

(75) Inventors: Georg Bretthauer, Karlsruhe (DE); Mark Bergemann, Göppingen (DE); Ulrich Gengenbach, Remchingen/Singen (DE); Torsten Koker, Stutensee (DE); Wolfgang Rückert, Wülfrath (DE); Rudolf F. Guthoff, Rostock (DE)

(73) Assignees: Forschungszentrum Karlsruhe GmbH, Karlsruhe (DE); Universitatsaugenklinik Rostock, Rostock (DE)

( * ) Notice: Subject to any disclaimer, the term of this patent is extended or adjusted under 35 U.S.C. 154(b) by 252 days.

(21) Appl. No.: 11/990,412

(22) PCT Filed: Jul. 31, 2006

(86) PCT No.: PCT/EP2006/064869
§ 371 (c)(1), (2), (4) Date: Mar. 11, 2008

(87) PCT Pub. No.: WO2007/020184
PCT Pub. Date: Feb. 22, 2007

(65) Prior Publication Data
US 2009/0105817 A1    Apr. 23, 2009

(30) Foreign Application Priority Data
Aug. 16, 2005   (DE) .......................... 10 2005 038 542

(51) Int. Cl.
*A61F 2/16*    (2006.01)
(52) U.S. Cl. ..................... 623/6.11; 623/6.22; 623/6.37
(58) Field of Classification Search ........ 623/6.11–6.64; 351/200; 200/85 R
See application file for complete search history.

(56) References Cited

U.S. PATENT DOCUMENTS 4,345,070 A    8/1982   Suarato et al.
(Continued)

FOREIGN PATENT DOCUMENTS

DE    43 00 840    7/1993
(Continued)

OTHER PUBLICATIONS

H. Schneider, O. Stachs and R. Guthoff, Evidenzbasierte Betrachtungen Zu Akkommodativen Kunstlinsen [= Evidence-Based Considerations About Accommodative Artificial Lenses], Lecture Delivered At the 102nd Annual Meeting of the German Ophthalmological Society, Held in Berlin on Sep. 23-26, 2004.

(Continued)

*Primary Examiner* — David H Willse
*Assistant Examiner* — Tiffany Shipmon
(74) *Attorney, Agent, or Firm* — Lucas & Mercanti, LLP; Klaus P. Stoffel (57) ABSTRACT

The invention relates to a device for restoring the accommodating ability of the eye, which comprises:
a) at least one optical system (3)
b) at least one data acquisition system (8) that does not touch the ciliary muscle and has either acoustic or optical means to detect the movement of the ciliary body, or it has means to detect the spatial orientation of the two eyeballs with respect to each other, or it has means for measuring the diameter of the pupil and the luminance in at least one eye as a physiological control signal for accommodation
c) at least one data processing system to produce a regulating signal for the optical system from the physiological control signal received
d) at least one power supply system (10), and
e) at least one system for attachment (22).

29 Claims, 7 Drawing Sheets

U.S. PATENT DOCUMENTS

| | | | |
|---|---|---|---|
| 4,373,218 A | | 2/1983 | Schachar |
| 4,466,706 A | | 8/1984 | Lamothe, II |
| 4,601,545 A | * | 7/1986 | Kern .............................. 349/200 |
| 4,732,458 A | | 3/1988 | Zambelli |
| 5,005,577 A | * | 4/1991 | Frenkel ......................... 600/398 |
| 5,171,266 A | * | 12/1992 | Wiley et al. ................... 623/6.22 |
| 5,593,437 A | * | 1/1997 | Arita et al. .................... 623/6.22 |
| 6,096,078 A | | 8/2000 | McDonald |
| 6,120,538 A | | 9/2000 | Rizzo, III et al. |
| 6,200,342 B1 | * | 3/2001 | Tassignon .................... 623/6.37 |
| 6,493,151 B2 | | 12/2002 | Schachar |
| 6,533,813 B1 | * | 3/2003 | Lin et al. ...................... 623/6.37 |
| 6,619,799 B1 | | 9/2003 | Blum et al. |
| 6,638,304 B2 | * | 10/2003 | Azar ............ 623/6.22 |
| 2002/0149743 A1 | | 10/2002 | Portney |
| 2004/0054407 A1 | * | 3/2004 | Tashiro et al. ............... 623/6.22 |
| 2004/0100704 A1 | | 5/2004 | Shadduck |
| 2004/0102843 A1 | * | 5/2004 | Yagi ............................... 623/4.1 |
| 2004/0181279 A1 | | 9/2004 | Nun |
| 2006/0136055 A1 | * | 6/2006 | Michel ......................... 623/6.37 |

FOREIGN PATENT DOCUMENTS

| | | |
|---|---|---|
| DE | 100 62 218 | 7/2001 |
| DE | 201 11 320 | 11/2001 |
| DE | 94 22 429 | 2/2002 |
| DE | 101 25 829 | 11/2002 |
| DE | 101 39 027 | 2/2003 |
| DE | 101 55 345 | 12/2003 |
| DE | 102 44 312 | 4/2004 |
| JP | 2001230004 | 8/2001 |
| WO | 99/18456 | 4/1999 |
| WO | 02/083033 | 10/2002 |
| WO | 03/017873 | 3/2003 |
| WO | 03/069380 | 8/2003 |
| WO | 2004/004605 | 1/2004 |

OTHER PUBLICATIONS

J. Kammann and G. Dornbach, Empirical Results Regarding Accommodative Lenses, In: Current Aspects of Human Accommodation, Ed. by R. Guthoff and K. Ludwig, Published by Kaden Verlag, Heidelberg, 2001, See pp. 163-170.

H. Fine, M. Packer and R. Hoffmann, Technology Generates IOL With Amplitude of Accommodation, In: Ophthalmology Times Special Report, Mar. 15, 2005.

M. Lavin, Multifocal Intraocular Lenses, Part 1, Optometry Today, No. 5 (2001), pp. 34-37.

M. Lavin, Multifocal Intraocular Lenses, Part 2, Optometry Today, No. 8 (2001), pp. 43-44.

O. Nishi, K. Nishi, C. Mano, M. Ichihara and T. Honda, Controlling the Capsular Shape in Lens Refilling, Archives of Ophthalmology, 115, No. 4 (1997), pp. 507-510, I.H. Fine, The Smartlens—A Fabulous New IOL Technology, Eye World, 7 No. 10 (2002.

Grote—Feldhusen (Eds.): Dubbel-Taschenbuch Für Den Maschinenbau [= Dubbel's Pocketbook for Machine Construction], 21st Ed., Published by Springer Verlag, Berlin—Heidelberg—New York, 2005.

O. Stachs, Monitoring the Ciliary Muscle During Accommodation, In: Current Aspects of Human Accommodation, Part II, Ed. by R. Guthoff and K. Ludwig, Published by Kaden Verlag, Heidelberg, 2003, See pp. 105-118.

E. Lütjen-Drecoll, Morphology and Age-Related Changes of the Accommodation Apparatus, In: Current Aspects of Human Accommodation, Ed. by R. Guthoff and K. Ludwig, Published by Kaden Verlag, Heidelberg, 2001, See pp. 25-35.

M. Joos, M. Rötting and B.M. Velichkovsky, Die Bewegungen Des Menschlichen Auge—Fakten, Methoden, Innovative Anwendungen [= The Movements of the Human Eye—Facts, Methods and Innovative Applications].

T. Hermann, S. Deutsch and G. Rickheit, Entitled "Handbuch Für Psycholinguistik" [= Manual of Psycholinguistics], Published by De Gruyter, Berlin—New York, 2002, See pp. 142-168.

J. Draeger and R.F. Guthoff, Kunstlinsenimplantation [= Implantation of Artificial Lenses], In: Augenheilkunde In Klinik Und Praxis [= Ophthalmology in Clinics and Practice], vol. 4, Edited by J. François and F. Hollwich and Published by Georg Thieme Verlag, Stuttgart—New York, 1991.

G.U. Auffarth and D.J. Apple, Zur Entwicklungsgeschichte Der Intraokularlinsen [= History of the Development of Intraocular Lenses], Ophthalmologie, 98 No. 11 (2001), pp. 1017-1028.

* cited by examiner

Figure 4:
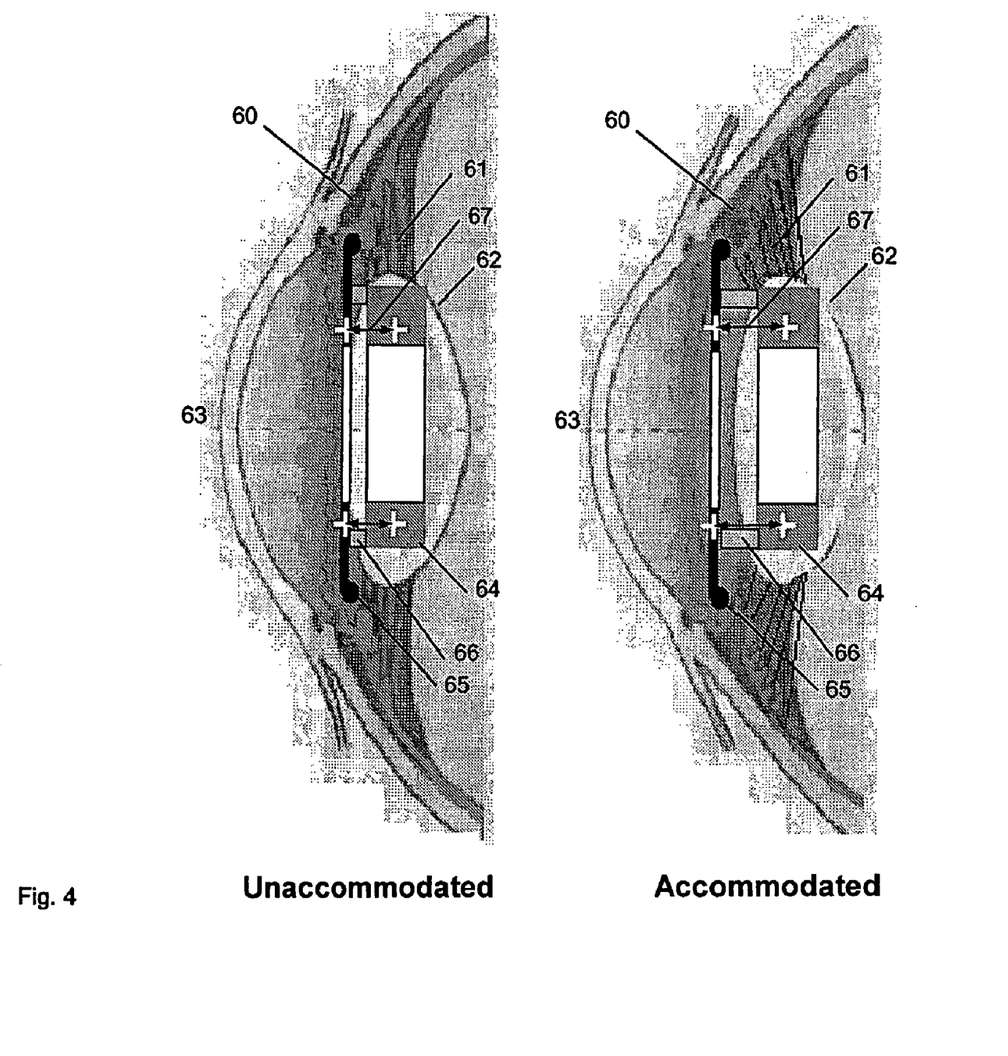

Fig. 4    Unaccommodated        Accommodated

OPTICAL DEVICE FOR RESTORING ACCOMMODATIVE CAPACITY OF THE EYE

The present invention relates to an implantable artificial accommodation system according to the first patent claim. The implantation of an artificial accommodation system into the human eye can restore the accommodative capacity lost either because of age-related presbyopia, i.e. old-age vision, or because of a cataract operation.

The human eye is an optical system that forms a sharp image of objects on the retina with the aid of a number of refractive interfaces. In doing so, the light waves pass through the cornea, the aqueous humour in the anterior chamber (camera anterior bulbi), the crystalline lens (lens crystallina) and the vitreous body in the posterior chamber (camera vitrea bulbi), which all have different refractive indices. If the distance from the object viewed changes, the imaging behaviour of the optical system must also change in order to ensure that an image with the same sharpness is formed on the retina. The human eye does this by altering the shape of the lens with the aid of the ciliary muscle (musculus ciliaris), as a result of which the shape and position of the anterior and posterior surfaces of the lens are basically changed, which is called accommodation. In the case of the intact accommodation system of a young person, the vertex power or vergency of the system can change in this way between the remote setting (unaccommodated state) and the near setting (accommodated state) by 14 dioptres, which is the range of accommodation. As a result, objects that are projected on the retina of young people with normal eyesight (emmetropic subjects) are in focus over the whole range extending from the far point, which is at infinity, to the near point, which is about 7 cm in front of the cornea.

The accommodative capacity of the human eye decreases with age and is completely lost after about 50 years of age, producing presbyopia, with an accommodation range of zero dioptres. Owing to the loss of accommodative capacity, the human eye cannot form sharp images on the retina any longer in the case of objects situated near the person, i.e. less than a meter away. We do not know yet fully the reasons for the decrease and loss of the accommodative capacity, but the essential factors are a decrease in the elasticity of the lens or phacosclerosis (lentis sclerosis) and possibly also a decrease in the ability of the ciliary muscle to contract.

The accommodative capacity is also lost when the opaque human lens is replaced by a rigid artificial lens in a cataract operation.

A number of implantable artificial lens systems with variable focal length have been developed in view of the above facts concerning presbyopia and cataract operation.

The potentially accommodative intraocular lenses are lenses or lens systems that are inserted into the eye to replace the natural lens after it is removed by surgery, and which are mostly fixed in the capsular sac. Under the influence of a still present but weak residual contraction of the ciliary muscle, an axial displacement of the lens is thought to be achieved here by a haptic.

An accommodative intraocular lens for implantation in the human eye is described for example in German Patent No. 94 22 429 U1. This has a monolithic lens body with regulating elements arranged on its circumference, which are directly connected with the ciliary muscle of the eye. For accommodation, the lens body is moved by the ciliary muscle to and fro within the eye via the regulating elements.

Implantable monolithic lenses that can be adjusted by the ciliary muscle via the regulating elements have also been described in German Patent Nos. 201 11 320 U1 and No. 100 62 218 A1. In this case, the regulating elements are elastic elevators, which define an initial rest position of the lens when not in operation.

German Patent No. 101 39 027 describes an intraocular lens with preferably four haptics that radiate outward and are flexibly connected to the optical system. When the ciliary muscle contracts, the lens is supposed to be displaced forward axially in the light path with the aid of the guide mechanism, thereby increasing the refractivity of the entire system.

Such implants have so far produced an axial displacement of the lens by at most 300-500 µm, restoring an accommodation of 1-2 dioptres. The distance of objects at which the image on the retina is still in focus is then about 50-70 cm in the case of persons with normal sight (emmetropic subjects). However, this is not sufficient, because an accommodation of more than 3 dioptres is needed for near vision, e.g. for reading. For this, the axial displacement produced under the influence of the ciliary muscle would have to be at least 2 mm, which is not possible for anatomical reasons. See H. Schneider, O. Stachs and R. Guthoff, Evidenzbasierte Betrachtungen zu akkommodativen Kunstlinsen [=Evidence-based considerations about accommodative artificial lenses], lecture delivered at the 102nd Annual Meeting of the German Opthalmological Society, held in Berlin on 23-26 Sep. 2004. See also J. Kammann and G. Dornbach, Empirical results regarding accommodative lenses, In: Current Aspects of Human Accommodation, ed. by R. Guthoff and K. Ludwig, published by Kaden Verlag, Heidelberg, 2001, see pages 163-170.

International Patent WO 02/083,033 describes a lens in the case of which the contraction of the ciliary muscle is supposed to displace a number of lens segments over one another via the deformation of the capsular sac. German Patent No. 101 25 829 A1 describes a lens in the case of which the radii of curvature of a sheath filled with a transparent material are supposed to change under the influence of the ciliary muscle on the capsular sac. However, neither of the last two solutions have yet been tried clinically.

However, all the systems mentioned above require an intact ciliary muscle and a deformable capsular sac for accommodation. If the ciliary muscle works only partly or not at all, e.g. if the capsular sac has become rigid due to capsular fibrosis, these systems cannot function well, if at all.

US Patent Application No. 2004/0,181,279 A1 describes a deformable lens that does not require the capsular sac to be deformable. In this case, the axial force operating through the movement of the ciliary muscle between the capsular sac that is rigid but can still be moved by the zonular fibres, and a firmly fixed plate placed outside the capsular sac is supposed to press a transparent deformable body into an orifice in this plate in such a way that the radii of curvature of the transparent deformable body are changed inside this orifice. However, an increased vertex power would only be expected in the case of a relaxed ciliary muscle if the zonular fibres tensed the capsular sac. A physiological adaptation, i.e. a learning process to tense the ciliary muscle for near vision would therefore be needed here. New designs that eliminate this problem have been promised in the literature. See H. Fine, M. Packer and R. Hoffmann, Technology generates IOL with amplitude of accommodation, In: Opthalmology Times Special Report, 15 Mar. 2005. However, this solution has not been shown to be applicable clinically either.

Multifocal correction divides the incident light into at least two focal points. This division can be based either on refractive or on diffractive elements, according to whether it involves breaking or bending the light, and it can be carried out either with rotational symmetry or in a segmented form.

US Patent Application No. 2002/0,149,743 describes a multifocal intraocular lens that splits the incident light into a number of focal points, so that a far sight and a near sight are supposed to be produced.

Although after a learning period patients generally tolerate that at least two images are superimposed on their retina, and they learn to direct their conscious observation to the sharp image, a reduction of the contrast sensitivity at the focal points is inevitable, and so is an increased dazzle sensitivity in the case of point sources of light. See M. Lavin, Multifocal intraocular lenses, Part 1, Optometry Today, No. 5 (2001), pp. 34-37. See also M. Lavin, Multifocal intraocular lenses, Part 2, Optometry Today, No. 8 (2001), pp. 43-44.

Another method, which is still in the animal experiment stage, involves the filling of the lens capsule with a polymer that polymerizes under the influence of light (lens refilling). See O. Nishi, K. Nishi, C. Mano, M. Ichihara and T. Honda, Controlling the capsular shape in lens refilling, Archives of Opthalmology, 115, No. 4 (1997), pp. 507-510. See also I. H. Fine, The SmartLens—a fabulous new IOL technology, Eye World, 7 No. 10 (2002).

However, it is difficult to find a suitable polymer for lens refilling that meets the requirements for elasticity, speed of polymerization, refractive index, transmission performance, biocompatibility and the absence of water absorption. Another problem concerns the control of the required refractive power during injection and polymerization. Since the capsular sac undergoes mechanical stiffening (capsular sac fibrosis) after the removal of the natural lens, it is doubtful whether the strength and mobility of the ciliary muscle are sufficient to bring about a suitable deformation of the refilled capsule.

Complete technical systems have also been proposed that aim at the re-establishment of the accommodative capacity, but these artificial accommodation systems have similarly not been tested clinically yet.

U.S. Pat. No. 6,120,538 describes an intraocular lens with microelectronic components mounted on its circumference. An example of its use relates to an artificial accommodation system that consists of a deformable lens with a band looped around it and an actor that can change the length of this loop and therefore produce a deformation in the lens. The signals are derived from the measurement of the axial distance of the object of fixation or from the observation of the sharpness of the image on the retina. The refractive power of the system is continuously adjusted to the requirements with the aid of a closed control circuit. A photodiode array is used to provide power for the system.

The solution proposed in this last U.S. Pat. No. 6,120,538 replaces both the retina as a natural sensor, and the natural neuronal information processing function of the brain. Its disadvantage is that a distance sensor must be positioned outside the light path in order to determine the distance from the object of fixation. Alternatively, a similarly implanted image acquisition sensor can be used, but this seems unrealistic in view of the limited space available for such a construction. For observing an image on the retina, a relatively calculation-intensive autofocus algorithm is needed to maximize the sharpness of the image. Furthermore, the retina is not an ideal artificial imaging screen but rather a multi-layer tissue composed of photoreceptors, nerve cells and blood vessels.

German Patent No. 101 55 345 C2 describes an intraocular lens with electrode structures arranged on its frame, which are supposed to establish electrical contact with the annular ciliary muscle in order to determine the correct (theoretical) value for the state of accommodation. The latter is converted in a closed control circuit into a regulating signal either for a lens with a variable focal length, or for a lens that can be axially displaced by an actor in the light path (closed control circuit). The power supply for remote transmission can be provided by a rechargeable energy storage device such as a battery or a condenser.

A disadvantage of this solution is that it is difficult to establish electrical contact with the ciliary muscle. When the artificial accommodation system is implanted in the capsular sac, the latter must be expected to act as an electrical insulator, so that it is impossible to receive sufficiently useful signals. The ciliary muscle itself is not accessible through the zonular fibre apparatus, and the removal of the zonular fibres and the capsular sac is incompatible with the quality standards of cataract surgery, since it risks the destabilization of the vitreous body. It must be assumed that in the fissure between the iris and the ciliary body (sulcus ciliaris or ciliary sulcus), no muscle activity is measurable by surface electrodes e.g. via a ring inserted there.

U.S. Pat. No. 6,096,078 describes an intraocular lens that is implanted into the ciliary sulcus to supplement a conventional intraocular lens, and which is supposed to be axially displaceable by the movement of the ciliary muscle. It also has sensors to detect information (data) about the physical state of the lens, especially the mechanical tension in the haptic. This information is transmitted to an external evaluating unit via an electrical connection located on the circumference of the lens or on the haptics. The subject of this U.S. Pat. No. 6,096,078 does not include the concept of a closed control circuit but merely offers the possibility of detecting the activity of the ciliary muscle.

U.S. Pat. No. 6,638,304 describes an intraocular lens which is made of an electro-optical material (liquid crystals), is fitted with electrode structures, and alters the imaging behaviour of the optical system. The information is obtained either by measuring the distance from the object of fixation (autonomic autofocus) or by using biological signals, which includes the following: registration of the signals that control the accommodation, namely the perception of the mechanical action of the ciliary muscle via a pressure sensor, the detection of the electrical activity of the ciliary muscle by surface electrodes, the detection of the tension in the zonular fibres, and the detection of the deformation of the capsular sac. The inventors suggest that the control signals of the iris contraction can be registered. They also mention the registration of the control signals of vergence, for which the contraction of a single external eye muscle (musculus rectus) is supposed to be detected mechanically, or else its neuronal innervation is to be detected electrically. A closed control circuit is achieved with the aid of a microcontroller. The power can be supplied by a battery or a photocell.

According to this last U.S. Pat. No. 6,638,304, the mechanical action of the ciliary muscle must be detected with the aid of a pressure sensor outside the capsular sac. However, as mentioned before, the ciliary body is not freely accessible through the zonular fibres. The detection of the electrical activity of the ciliary muscle by means of surface electrodes is difficult, owing to the poor accessibility and electrode passivation that occurs. No feasible solution of this is suggested in this US patent. Since the capsular sac stiffens due to capsular sac fibrosis after the natural lens is removed, the detection of the deformation of the capsular sac cannot be used as a source of information. The use of the iris contraction alone as a source of information is also unsuitable, because it is not connected to accommodation in a straightforward manner. The diameter of the pupil varies not only with the pupillary near reflex but also with the pupillary light reflex.

By contrast, there is a straightforward connection between the need for accommodation and the oculomotor activity. For this, the orientation of the lines of fixation of both eyes must be determined. It is not sufficient to detect the electrical or mechanical activity of the horizontal eye muscles of just one eye for determining the orientation of the lines of fixation of both eyes, because not only vergences occur (rotation of the eyes in the opposite direction) but also versions (their rotation in the same direction). Accordingly, to determine the (horizontal) vergence, we have to detect the difference in the angle of yaw of both eyes, or alternatively determine the two angles of yaw separately, and then form a difference from them. However, this is not mentioned in this US patent.

International Patent WO 2004/004,605 describes an artificial accommodation system consisting of two deformable spherical lenses for both eyes, each of which has a band looped around it and each has an actor that can change the length of loop and so produce a deformation of the lens, and each has a microcontroller, each of which produces a control signal, as well as an information system based on the measurement of the vergence movement. The surface compression at the interface is detected by pressure sensors that are located between the nasal or temporal horizontal external eye muscle (musculus rectus medialis or musculus rectus lateralis) and the eyeball. The assumption made here is that pressure is generated on the side opposite the sensor only when the eyeball is being rolled. A control signal is then only sent if both sensors detect a pressure, i.e. when both eyeballs execute a rotational movement inward. The implant is supplied with power from the outside.

In International Patent WO 2004/004,605, the element influencing the imaging behaviour is a spherical elastic lens that is supposed to be modified in its curvature by a band looped around it. No other possibility is mentioned for influencing the imaging characteristics that could be used to save space and power. The implantation of the pressure sensors below the external eye muscles involves the risk of tissue fibrosis, connected with tissue stiffening and the encapsulation of the sensor, making the measurement of pressure impossible. Furthermore, it is assumed here that the object of fixation is central in the field of vision, so that both eyeballs perform an inward rotation to the same extent. However, there is generally a superposition of conjugated eye movements (versions) and disjointed ones (vergences). If the object of fixation does not lie centrally in the field of vision, the two eyes have different angles of yaw, so we do not necessary have an inward rotation of both eyeballs. The effect of vertical movements ("nodding" movements) of the eyeballs on the need for accommodation is not taken into account here.

Devices for the restoration of the accommodative capacity are also known from the following publications: German Patent No. 101 55 345 C2, U.S. Pat. No. 6,638,304 B2, International Patent WO 03/017,873 A1 and U.S. Pat. No. 4,372,18.

On the basis of all this, the task of the present invention is to provide an implantable artificial accommodation system whose control mechanism does not depend on the ciliary muscle as the regulating element influencing the optical imaging behaviour, though the ciliary muscle can be used as a source of information for determining the need for accommodation.

This task is achieved by the following accommodation system:

it comprises an optical system that contains at least one active optical element and/or at least one rigid lens (passive optical element) that can be displaced axially by at least one actor it has at least one data acquisition system, which:
can be used without any mechanical or electronic contact with the ciliary muscle, detects the residual activity of the ciliary muscle either directly but without contact or indirectly by registering either the tension in the anterior tendon of the ciliary muscle in the ciliary sulcus or its effect on the surrounding tissues, or indirectly via the axial displacement of the whole capsular sac with respect to a stationary point outside the capsular sac or it uses the connection between the need for accommodation and the pupillary near reflex by determining the diameter of the pupil and the absolute luminance or it uses the connection between the need for accommodation and the movement of the pair of eyes by determining the spatial orientation of the two eyeballs either fully or partly at least one data processing system at least one power supply system, and at least one system for attachment.

In particular, the invention relates to a device for restoring the accommodative capacity of the eye, which comprises:

a) at least one optical system b) at least one data acquisition system that does not touch the ciliary muscle and which uses either acoustic or optical means to detect the movement of the ciliary body, or has means to detect the spatial orientation of the two eyeballs with respect to each other, or has means for measuring the diameter of the pupil and the luminance in at least one eye as a physiological control signal for the accommodation c) at least one data processing system to produce a regulating signal for the optical system from the physiological control signal received d) at least one power supply system, and e) at least one system for attachment.

The various sub-systems are connected here to one or more control circuits. The optical system, the data acquisition system, the data processing system, the power supply system and the system for attachment are preferably combined in an implant that can be inserted in the human or animal eye with the aid of the system for attachment to restore its accommodative capacity. The optical system is arranged here in the light path of the eye and forms, in combination with the latter, the dioptric apparatus of the eye. In the same way, the data acquisition system, the data processing system and the power supply system are preferably arranged outside the light path. The data acquisition system can be divided over a number of implants, e.g. in the left and right eyeball or in the maxilla. The power supply system can preferably be connected to an external system without the use of a wire.

The optical system, which comprises one or more active optical elements and/or one or more rigid lenses (passive optical elements) that can be displaced by actors, has the task of influencing the imaging behaviour in the light path. It must be transparent in the visible wavelength region, and the position and/or shape of at least one of its refractive interfaces must be capable of changing in the course of time in order to alter the vertex power of the dioptric apparatus. The actor component consists here of power regulators and power transformers, which exert a force under the influence of the regulating signals of the data processing device, which power can then be converted into movement. See Grote—Feldhusen (eds.): Dubbel-Taschenbuch für den Maschinenbau [=Dubbel's Pocketbook for Machine Construction], 21st ed., published by Springer Verlag, Berlin—Heidelberg—New York, 2005.

In the case of the passive optical element, the actor displaces one or more rigid lenses axially in the light path. This operating principle is routinely used in technical products used for focussing. German Patent No. 43 00 840 A1 describes e.g. a vario-objective for compact cameras that consists of two lens groups, where the distance between them can be varied to adjust the focal length.

Various mechanisms can perform the above-mentioned task of the active optical element. We must distinguish here between a change in the refractive index distribution and a change in the curvature of an interface that separates two media with different refractive indices. These changes can be brought about on the basis of various physical operating principles, which are described below.

Changing the Refractive Index by the Use of Electro-optical Materials:

The birefringent characteristic of electro-optical materials can be altered by an electromagnetic field. This can give a well-defined refractive index distribution, which makes it possible to influence the imaging behaviour in one polarization plane of the light in a specific way. This can include not only the required change in the position of the focus, but also the correction of higher-order imaging errors, such as for example astigmatisms, spherical aberrations and the optical aberration known as coma. Two such systems must be placed one behind the other and arranged cross-wise at right-angles in order to affect equally the two polarization planes that are vertical to each other. U.S. Pat. No. 6,619,799 describes the use of such an active optical element in the frame of spectacles. The electro-optical layer is surrounded here by two transparent electrode surfaces, between which an electrical potential can be applied in order to change the radial refractive index profile. The required refractive index profile can be obtained either by amplitude and frequency modulation of the control voltage or by distributing the electrodes over a number of regions, each fed with a different voltage.

Changing the Refractive Index by Varying the Density of a Compressible Fluid:

The refractive index of a compressible fluid such as a gas or a mixture of gases depends on its density, this variation being given by the Gladstone-Dale constant. If the pressure and/or temperature are changed in a gas-filled chamber having one or more curved interfaces, the imaging behaviour of the optical system changes accordingly. U.S. Pat. No. 4,732,458 describes e.g. such an arrangement for a multi-lens element whose refractive power can be changed continuously. The pressure is increased in the rigid gas-filled chamber by a movable piston inside a cylinder, mounted outside the optical axis.

Changing the Geometry by Exerting an Outside Force on an Elastic Solid Body:

An elastic solid whose refractive index is different from that of the surroundings can be deformed by an outside force in such a way that the curvature of its light refracting surfaces is altered, and so its optical imaging behaviour is changed. U.S. Pat. No. 6,493,151 describes e.g. an arrangement for such a homogeneously or inhomogeneously constructed deformable solid body to which radial forces can be transmitted via a ring whose diameter can be changed. The diameter of the ring can be changed by thermal means or with the aid of a magnetic or electrical field. German Patent No. 4,345,070 describes e.g. an arrangement for a deformable sheath-like solid body that is filled with a transparent liquid and whose light-refracting surfaces are deformed hydraulically or pneumatically by means of an annular fluid actor. German Patent No. 10 244 312 mentions as an example the use of an actor made of Bucky paper (a paper-like network composed of carbon nano-tubes) to change the refractive power of an artificial deformable lens implanted in the eyeball.

Changing the Geometry by Varying the Wetting Angle (Electro-wetting):

Two mutually immiscible fluids having approximately the same density but different refractive indices form a spherically curved or planar interface (meniscus). If one of them, which is an electrically conducting fluid, is brought into contact with an electrode, and a potential difference is applied between this electrode and a second one, which is separated from both fluids by an insulating layer (a dielectric), then the wetting angle and so the curvature of the meniscus can be changed by the electro-wetting effect. Since the meniscus separates two media with different refractive indices, the optical imaging behaviour is changed. International Patent WO 99/18,456 describes an axial arrangement of a conducting fluid, a transparent dielectric and a transparent electrode in the light path, together with means for the radial centering of the drop in the optical axis. International Patent WO 03/069,380 describes an arrangement in which an electrode coated with a dielectric is mounted cylindrically about the optical axis. The electrically conducting fluid, the insulating fluid and the meniscus separating them are arranged axially one behind the other in the optical axis.

Changing the Geometry by Altering the Pressure of a Fluid:

If the pressure difference from the surroundings is changed in a chamber that is filled with a fluid and which has one or more deformable interfaces, then the curvature of the interfaces also changes, and so does therefore the imaging behaviour of the optical system. U.S. Pat. No. 4,466,706 describes e.g. such an arrangement, where the change in the pressure difference is effected by a displacing mechanism. In this case, the fluid is displaced by turning a screw mounted in a cylindrical envelope, which alters the curvature of both cylindrical surfaces. Alternatively, the cylindrical envelope can be made in two parts, and a displacement can be achieved by an axial movement of the two parts relative to each other.

Changing the Geometry by Exerting a Force Inside a Smart Material:

Smart materials can generate a force by changing their atomic or molecular structure and so they undergo deformation. The optical imaging behaviour can therefore be also altered by varying the interface profile between the smart material and its surroundings. US Patent Application No. 2004/0,100,704 describes e.g. a designer plastic used for this purpose, which is used as a layer or phase inside a deformable lens body and which can locally alter the shape of the body under the influence of an energy input. The patent in question mentions as an example of use the postoperative irreversible correction of the imaging behaviour of an implanted intraocular lens. Japanese Patent No. 01230004 describes for example the use of a swelling gel and a solvent, which are arranged in layers inside a deformable solid body. When a force is applied, the solubility of the solvent in the swelling gel can be changed in such a way that its volume changes as a result. This in turn alters the curvature of the light-refracting surface.

The above operating principles can also be combined with one another. The optical system can therefore adjust the focal position of the dioptric apparatus. Furthermore, the optical system can include several elements for optimizing the optical imaging behaviour in the light path. An active optical element in it can if necessary correct any further imaging errors (monochromatic and chromatic aberrations) either statically or dynamically (local effect of the light wave front).

To generate the regulating signals for the actor component of the active optical element or the passive optical element, it is necessary to collect information from which a decision can be made as to the necessary increase in the vertex power, i.e. as to the need for accommodation.

Information about the need for accommodation can be obtained both from the physiological control signal of accommodation and from the physiological control signals of the oculomotor activity. The term "control signal" means here information that contains, over a certain control range, the correct (theoretical) value or the actual value that is obtained from the theoretical value and any possible interference signals. The signal from one eye can be used as the control signal of accommodation (nerve signal, change in the potential of the ciliary muscle, or the movement of the ciliary muscle), because it contains all the information about the need for accommodation. However, if the oculomotor system is used for control signals, we must use information from both eyes and determine the need for accommodation in question.

The biological control signal of accommodation is generated by the Edinger-Westphal centre in the mid-brain, so that both eyes receive the same control signal in accordance with the principle of consensuality. The signal reaches the ciliary muscle of the left or right eye via the ciliary nerve in the parasympathetic nervous system, in the form of a pulse-like sequence of voltage fluctuations. The nerve acts on the ciliary muscle there (which is regarded as a smooth muscle) and makes the annular muscle contract by changing the calcium ion concentration in the muscle cells. This contraction of the ciliary body, which is characterized by a radial component towards the optical axis of the iris and an axial component away from the iris, can be used to obtain information about the need for accommodation in the eye in question, since the contractibility of the ciliary muscle is still in evidence in presbyopic patients, although it decreases with age. See O. Stachs, Monitoring the ciliary muscle during accommodation, In: Current Aspects of Human Accommodation, Part II, Ed. by R. Guthoff and K. Ludwig, published by Kaden Verlag, Heidelberg, 2003, see pp. 105-118. The ciliary body is separated from the lens contents by the capsular sac and the zonular fibre apparatus. It is therefore not accessible for a mechanical or electrical contact even after the contents of the lens have been removed in a cataract operation.

A contact-free acquisition of the movement of the ciliary body is therefore proposed as the source of information according to the present invention. This can be accomplished e.g. by measuring the distance from the peripheral region of an implant in the capsular sac either by an acoustic method (e.g. one that determines the difference in the ultrasound transmission time) or by an optical method.

Another possible source of information is represented by the change in the shape of the ciliary sulcus (sulcus ciliaris). The relatively stiff anterior tendons fix the ciliary muscle to the scleral fold and the trabecular network, so they experience a pull when the ciliary muscle contracts. See E. Lütjen-Drecoll, Morphology and age-related changes of the accommodation apparatus, In: Current Aspects of Human Accommodation, Ed. by R. Guthoff and K. Ludwig, published by Kaden Verlag, Heidelberg, 2001, see pp. 25-35. This tension in the tendon, or its effect on the surrounding tissues, can be detected e.g. by measuring the surface compression of a ring placed in the ciliary sulcus. This may, but need not be, part of the means whereby the implant is attached.

Another possible source of information is represented by the axial displacement of the capsular sac with respect to at least one point outside the capsular sac but inside the eye. When the ciliary muscle contracts, the diameter of this annular muscle decreases, and so does the tension in the zonular fibres. If the capsular sac in the unaccommodated state is pre-tensed in the axial direction either in the extension or in the compression mode, this movement causes an axial displacement of the whole capsular sac in the path of light. This displacement is connected with the need for accommodation in a straightforward manner. The necessary pre-tension can be achieved for example with the aid of an elastic material placed between the capsular sac and a plate that is positioned in the ciliary sulcus in front of the capsular sac and which is transparent in the middle. The relative axial movement is then determined e.g. by measuring the mechanical extension of the elastic material inserted. Another possibility for applying the necessary pre-tension is to use magnetic forces acting between a point in the capsular sac (e.g. in a part of the implant) and a point outside the capsular sac, e.g. in a plate that has a transparent middle and is positioned in the ciliary sulcus in front of the capsular sac. In this case, too, any measuring method that is physically possible (e.g. a contact-free optical distance measurement) can give the relative displacement between the two points.

The oculomotor activity (especially the horizontal vergence movement) and the need for accommodation are connected in a straightforward manner in the case of binocular vision. The lines of fixation of both eyes are directed, due to the rotation of the eyeballs, towards a given object of fixation anywhere in space in such a way that the image of the object in question impinges on the corresponding site on the retina. This makes it possible to merge the information from the two individual images in order to form a single picture in the brain. The spatial orientation of the eyeballs can also be described by the rotations of the eyeballs about the three spatial axes. We have here, separately for each eyeball, rotations about the vertical axis (yawing movements), rotations about the co-extensive horizontal axis (nodding movements), and rotations about the co-extensive line of fixation (rolling movements). We can accordingly distinguish, for both eyes, conjugated eye movements (versions, i.e. movements of the lines of fixation or the retinal meridians of both eyes, which movements are identical in magnitude and direction), and disjointed eye movements (vergences, i.e. movements of the lines of fixation or the retinal meridians of both eyes, which movements are identical in magnitude but opposite in direction). In general, there is a slight difference in the distance of the object of fixation from the two mechanical oculogyric points, and so also in the need for accommodation, especially if the object of fixation is not symmetrical with respect to and near the two eyes. The control signals from the oculomotor activity (nerve signals or muscle signals) can be detected outside the body (e.g. by electromyography of the eye muscles), but their intracorporeal detection would be complicated. The motor aspects of the eye movements are very precise even in advanced age, and the deviations between the theoretical and the actual values (fixation disparity) only amount to a few minutes of an angle. This ensures, in the case of binocular vision, a section of the lines of fixation as a very good approximation, and a conclusion can be drawn from the effects of the nerve signals and muscle signals on the ocular motor performance, i.e. from the orientation of the two eyeballs in space, as to the need for accommodation in the left or right eye.

The extracorporeal methods for measuring the spatial orientation include e.g. magnetic induction, in the case of which contact lenses fitted with a coil are applied to the cornea of the patient, or the coils are implanted directly, and the spatial orientation is inferred from the induced voltage in an alternating magnetic field. Another extracorporeal measuring method is based on a video technique, in which the spatial orientation is inferred by observing the pupils, the corneal reflex or the limbus. See M. Joos, M. Rötting and B. M. Velichkovsky, Die Bewegungen des menschlichen Auge—Fakten, Methoden, innovative Anwendungen [=The movements of the human eye—facts, methods and innovative applications], In a book edited by T. Hermann, S. Deutsch and G. Rickheit, entitled "Handbuch für Psycholinguistik" [=Manual of Psycholinguistics], published by De Gruyter, Berlin—New York, 2002, see pages 142-168. According to the present invention, the spatial orientation can be determined with respect to a reference system, with the head being fully or partly fixed (fixed-head reference system) by measuring the distance between the various reference points. A fixed-head reference system consists of a set of coordinates in which the position of the two mechanical oculogyric points does not change in the course of time. The need for accommodation can again be determined from the orientation measured.

The spatial orientation of the two eyeballs is ideally determined accurately by measuring the distance between a) one or more fixed-eyeball points lying eccentrically to the mechanical oculogyric point and b) one or more fixed-head reference points. The fixed-eyeball points can also be located both inside the eyeball (e.g. on the artificial accommodation system) and on its external surface (e.g. on a contact lens that moves with the eyeball, or directly below the insertion of an external eye muscle, such as the musculus rectus lateralis, the musculus rectus medialis, the musculus rectus superior, the musculus rectus inferior, the musculus obliquus inferior or the musculus rectus obliquus superior). The fixed-head reference points are points whose spatial position does not change in the fixed-head reference system in the course of time (e.g. a cheekbone or the maxilla, but not the mandible).

This method also gives the exact need for accommodation of the left and right eye. However, a sufficiently accurate approximation of the need for accommodation can also be obtained by using fewer fixed-eyeball and/or fixed-head reference points, and two possible arrangements for this are described below.

If only the distance between the two fixed-eyeball reference points on the left and right eyeball is determined, the result can be used as a measure of the need for accommodation in the left and right eye in the form of a single value in an approximation that is sufficiently accurate for practical purposes. In this case, the difference between the need for accommodation of the left eye and that of the right eye cannot be obtained, but then it is not possible in the case of the natural accommodation system either.

If we determine the distance between a fixed-eyeball point and a fixed-head reference point both on the left and on the right, as well as the distance between the two fixed-eyeball reference points, the three results thus obtained can be used to infer the need for accommodation of the left and right eye separately from each other. This gives a more accurate measure of the need for accommodation than the previous methods.

All suitable measuring methods can be used for determining the distance between the fixed-eyeball points with regard to each other and/or one or more fixed-head reference points. For example, we can determine as a measure the distance-dependent weakening of a stationary magnetic field, the difference in transit time, or the phase shift of an electromagnetic wave.

In the preferred configuration, both eye implants contain measuring systems consisting of transmitters and receivers. The fixed-head reference point is occupied by an object, and the distance between it and the implant is determined. Each eye implant measures both the distance from the partner-eye implant and the distance from this object in the fixed-head reference point, and communicates both values to the other eye implant. Therefore, each eye implant has three experimental values for distance measurement at its disposal, so that a mean value can be formed for the distance of the two fixed-eyeball points in order to reduce the experimental error.

To increase the reliability of data acquisition, redundant experimental values can be collected, e.g. by using several fixed-eyeball points for an eyeball.

As an alternative to the measurement of distances, the angles of yaw are preferably measured for both eyes with respect to the head by means of a suitable measuring system. The possibilities for this include e.g. the use of myoelectrodes for detecting the changes in the potential in the musculus rectus medialis or the musculus rectus lateralis, and the use of magnetoresistive sensors (XMR sensors) on the implant and a reference magnet on the orbital cavity.

Detecting the control signals from the diameter of the pupil alone is not sufficient for determining the need for accommodation, since the corresponding measurement depends on two unknown influencing factors, namely the luminance and the distance of the object. Another possible way to collect the necessary information is to determine simultaneously the diameter of the pupil, or the contraction/dilation of the iris, and the luminance in the light path, so that the pupillary near reaction can be separated from the pupillary light reflex. Since the posterior side of the iris is accessible from the capsular sac, the diameter of the pupil can also be determined by a technique that involves actual contact. Alternatively, we can use the differences in the luminance in a photodiode array positioned behind the iris. At the same time, the absolute value of the luminance of the incident light is determined preferably with the aid of a photodiode. The need for accommodation can therefore be inferred from the experimental value of the pupillary diameter and the absolute luminance.

The data collected in the present invention are placed at the disposal of the data processing system. However, the data acquisition system described above is in itself a subject of the invention, being capable of transmitting experimental values to an extracorporeal receiver for registering and further processing.

The signals detected are processed by a data processing system used e.g. for smoothing, filtering, amplifying and testing for outlier values. Methods of classical statistics, computational intelligence and data mining are used to extract and classify characteristics for detecting the intended accommodation. The required regulating signals for the optical system are generated by methods used in control and regulation techniques, such as fuzzy-controlled PID regulators, adaptive regulating algorithms and self-learning algorithms. Both hierarchical regulating structures and central/decentral structures can be employed.

The sub-systems are supplied with power from a power supply system that can consist of an energy transformer, an energy storage device and a control unit. The energy transformer converts energy that is remotely transmitted from outside (e.g. inductive, capacitive or optical) or the energy stored e.g. in batteries or miniature fuel cells, which can also be in the form of body fluids (e.g. nutrient-rich aqueous humour or blood), or it converts mechanical energy (e.g. from the movements of muscle) into electrical energy via an energy storage device. The required power is transmitted to the sub-systems through the control unit of the power supply system at precisely defined points in time. By measuring the luminance (e.g. with the aid of a photocell) we can ensure that the whole system is brought to a state in which the energy conversion is minimal when it is dark or the eyes are closed, i.e. in situations in which no accommodative capacity is needed. The control signals needed for this are generated by the data processing system.

The entire system is implanted by using suitable means of attachment for axial fixation and radial centering in the light path. Numerous haptic versions are known for intraocular lenses in opthalmology. See J. Draeger and R. F. Guthoff, Kunstlinsenimplantation [=Implantation of artificial lenses], In: Augenheilkunde in Klinik und Praxis [=Opthalmology in Clinics and Practice], vol. 4, edited by J. Francois and F. Hollwich and published by Georg Thieme Verlag, Stuttgart—New York, 1991. See also G. U. Auffarth and D. J. Apple, Zur Entwicklungsgeschichte der Intraokularlinsen [=History of the development of intraocular lenses], Opthalmologie, 98 No. 11 (2001), pp. 1017-1028. The intraocular lenses are preferably secured in the iridocorneal chamber angle, the ciliary sulcus or the capsular sac.

The artificial accommodation system according to the invention is the technical part of the control system (closed control circuit), which is an artificial system that takes over the function of the natural deformable crystalline lens and the ciliary muscle of a patient. The biological part essentially consists of the cornea, the aqueous humour and the vitreous body, as components of the dioptric apparatus, the retina as a natural sensor array, and the brain as a natural data processing unit that generates control signals containing information about the need for accommodation.

The artificial accommodation system comprises an optical system with adjustable focal length and/or other optical characteristics. This forms a newly introduced component of the patient's dioptric apparatus. It comprises a data acquisition system that preferably performs distance measurements between fixed-eyeball and fixed-head measuring points. These distance measurements are used by the data processing system to determine the need for accommodation and generate the regulating signals for controlling the optical system. The system is energized from a suitable power source and is fixed in the patient's eye with the aid of a system for attachment.

The essential underlying concept of the invention is a complete implantable system for the partial or complete restoration of the accommodative capacity, which system does not rely on the power of the natural actor (ciliary muscle) but instead:

1) it uses either the residual activity of the ciliary muscle by detecting its movement directly and without contact or indirectly via the change in shape of the ciliary sulcus (caused e.g. by the tension in the anterior tendon of the ciliary muscle) or indirectly via the axial displacement of the whole capsular sac with respect to a stationary point outside the capsular sac, in which case, it is possible to fit one of the eyes with an implant
2) or it uses the connection between accommodation and pupillary near reaction, where the need for accommodation is inferred from the experimental values for the diameter of the pupil and the absolute luminance, so that interference by the pupillary light reflex can be eliminated; in this case, it is possible to fit one of the eyes with an implant
3) it uses the connection between the need for accommodation and the movement of both eyes, without engaging the motor activity of the external eye muscles; in this case, the following applications are possible:
a) In the case of binocular implantation, an artificial accommodation system is implanted into both eyes. Points on each implant are preferably chosen as the fixed-eyeball reference points. The data acquisition systems of the two implants communicate with each other, so that information is obtained about the movement of the pair of eyes.
b) In the case of monocular implantation, only one of the eyes is fitted with an artificial accommodation system, and a point on the implant is preferably chosen as the fixed-eyeball reference point. However, a reference point on the other eye is also required for determining the need for accommodation. To eliminate the need to open the eyeball of unoperated eye, an auxiliary implant is applied preferably to the reference point that lies on the outer surface of the eyeball, which implant comprises at least one data acquisition system. The data acquisition systems of the implant and the auxiliary implant communicate with each other, so that information is obtained about the movement of the pair of eyes.

The accuracy of the approximation of the need for accommodation can be improved by using a fixed-head reference point both in monocular and in binocular implantation.

The system is capable of adjusting the focal position according to the changing distance of objects. This also provides a postoperative compensation of the refraction in the case of objects at infinity (far point). It is also possible to adjust the system repeatedly after operation, e.g. in the case of children in whom the required vertex power region changes as they grow.

When using a suitable optical system, we can also correct the higher-order aberrations, such as for example astigmatisms, spherical aberration and coma. These refraction deficits can be basically determined by the extracorporeal analysis of the wave front. The information thus obtained can be employed for correcting the light wave front at certain intervals of time.

By comparing the luminance with a threshold value, we can reduce the energy consumption of the whole system in a state in which no accommodation is needed.

The accommodation system described here can be used to restore the accommodative capacity after the removal of the natural crystalline lens for cataract or presbyopia.

The invention is described below in more detail with reference to the drawings.

Figure 1:
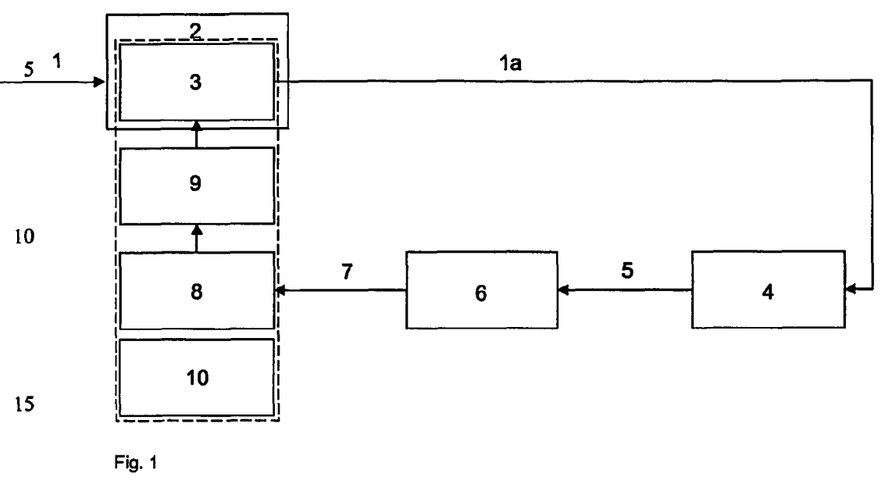

FIG. 1 shows a diagrammatic representation of the complete artificial accommodation system. The information 1, which can be e.g. light from an object, is received by the dioptric apparatus of the human eye 2 containing the optical system 3. The distance from the object can change in the course of time. The focussed light 1a impinges on the retina 4, which is a natural sensor.

The afferent signals 5 generated by the photoreceptors travel to the brain, which is the natural information processing system 6. The efferent signals 7, which contain information about the need for accommodation, are transmitted from the brain to the motor structures, such as for example the ciliary muscles and the muscles of the eyeballs. This information is received by the data acquisition system 8 of the artificial accommodation system. The data processing system 9 forms from this information the regulating signals for the optical system 3. As a result, the vertex power of the dioptric apparatus 2 is adjusted by the artificial accommodation system according to the need for accommodation, which is obtained from the distance of the object that can vary in the course of time (signal 1). The system is completed by a power supply system 10. All the technical parts of the system are placed inside a dotted-line box here.

Figure 2:
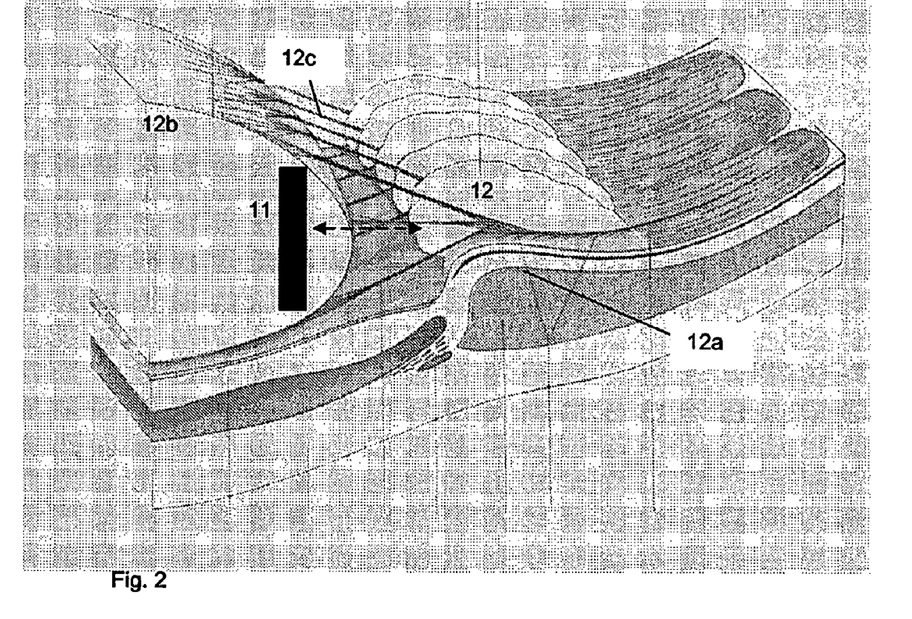

FIG. 2 shows an embodiment of the data acquisition system 8 in detail. The ciliary body 12 is not accessible for mechanical or electrical contact through the capsular sac 12b and the zonular fibres 12c. The activity of the ciliary muscle 12a, which is predominantly manifested in a radial displacement of the ciliary body 12, is detected by a contact-free distance-measuring system 11, which determines the distance from the ciliary body 12 at one or more points on the circumference.

Figure 3:
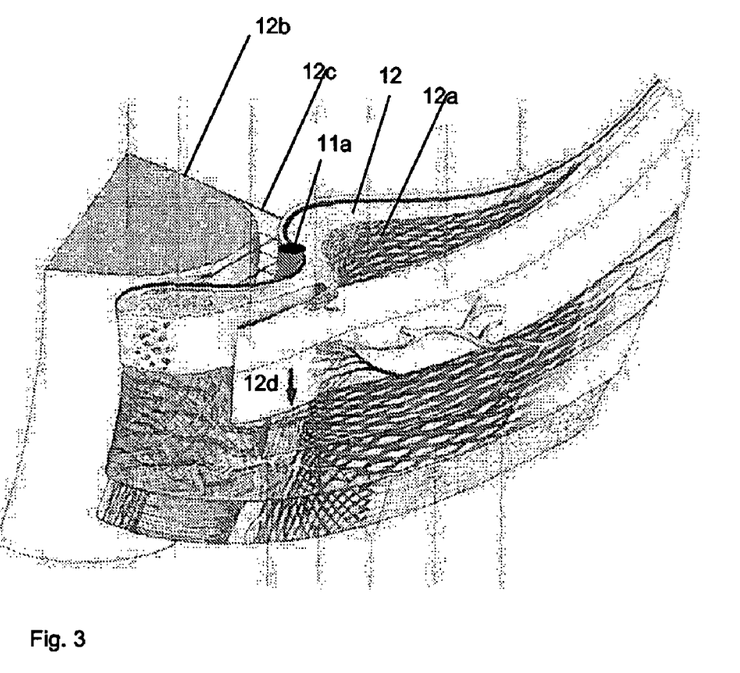

FIG. 3 shows another possible way of detecting the activity of the ciliary muscle. The activity of the ciliary muscle 12a is manifested not only in the displacement of the ciliary body 12 mentioned above, but also in a tension in the anterior tendon 12d of the ciliary muscle, which fixes the ciliary muscle in the scleral fold. This tension, or its effect on the surrounding tissues, is detected by a ring 11a, which is fitted with suitable sensors and inserted into the ciliary sulcus (a circular groove between the root of the iris and the ciliary villus). For a clearer illustration, the capsular sac 12b and the zonular fibres 12c are also shown in FIG. 3.

FIG. 4 shows another embodiment for detecting the activity of the ciliary muscle. The anterior section of the human eye is shown here in cross-section both in the unaccommodated state on the left and in the accommodated state on the right. The ciliary muscle 60 lying in the ciliary body forms a ring around the optical axis 63. The capsular sac 62 is suspended over the zonular fibres 61. The part of the data acquisition system that lies in the capsular sac 62 is indicated by 64. The part of the data acquisition system that lies outside the capsular sac 62 is indicated by 65. If there is, acting between the two parts, e.g. a repulsive force (for example a magnetic force or a force of restitution of a pre-tensed elastic intermediate body 66 (though an attractive force is also possible), then the capsular sac 62 is displaced axially and towards the rear (shown on the right) when the ciliary muscle 60 contracts to acquire a smaller annular diameter. This increases the distance 67 between the two components of the data acquisition system 64 and 65 in comparison with the relaxed state of the ciliary muscle (on the left), which is accompanied by a larger annular diameter. By determining the changing distance, we can obtain information about the state of contraction of the ciliary muscle, and so about the need for accommodation.

Figure 5:
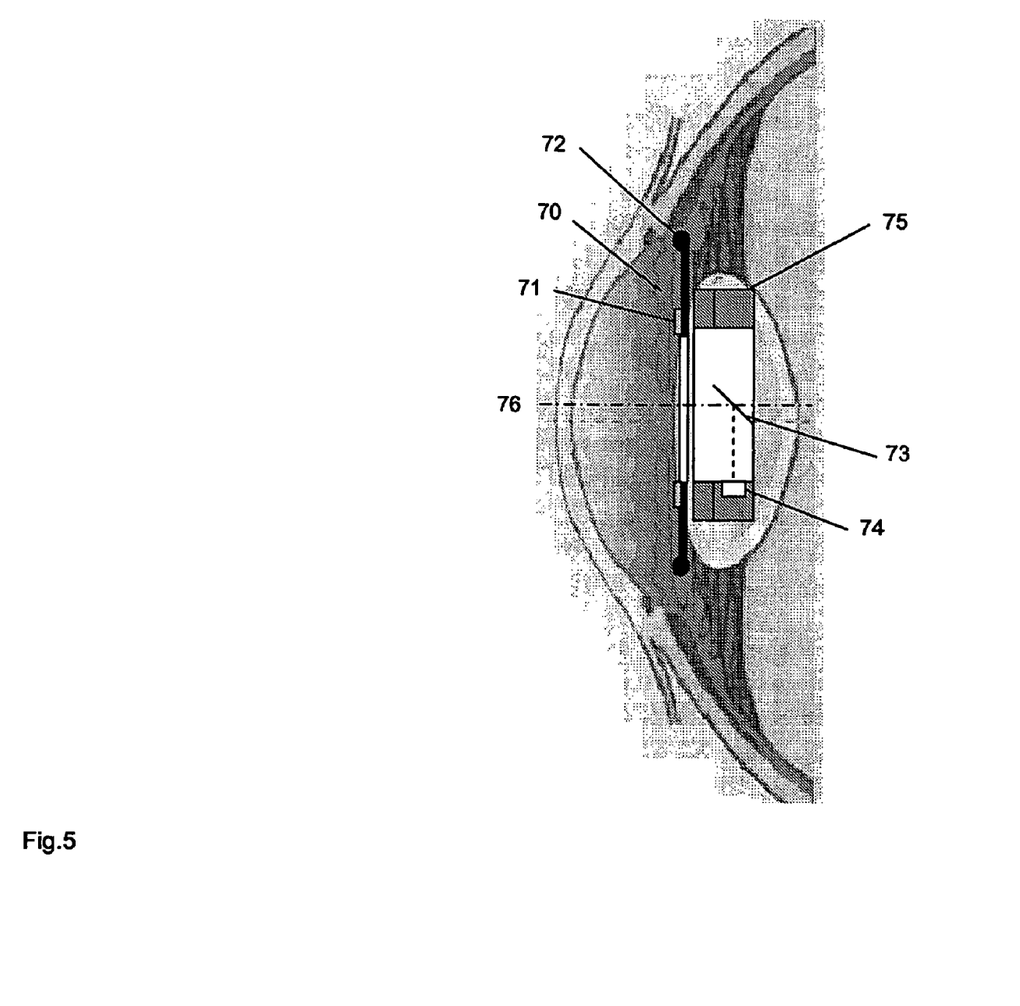

FIG. 5 shows an embodiment of the data acquisition method according to the invention, in which the connection between the need for accommodation and the pupillary near reaction is utilized. For this purpose, the contraction of the iris muscle 70 is detected by a sensor 71 in a way that involves contact. This sensor is placed on a component of the system for attachment 72 (here inserted in the ciliary sulcus), so that a relative movement between the sensor and the iris occurs. At the same time, the absolute value of the luminance is determined by a photocell 74. For this purpose, a suitable light-deflecting element 73 can be mounted in a part of the light path, which however does not inhibit the optical imaging on the retina along the optical axis 76. The light-deflecting element 73 and the photocell 74 can, but need not, be mounted on an attachment structure 75, which is fixed in the capsular sac here and is different from the system for attachment 72.

Figure 6:
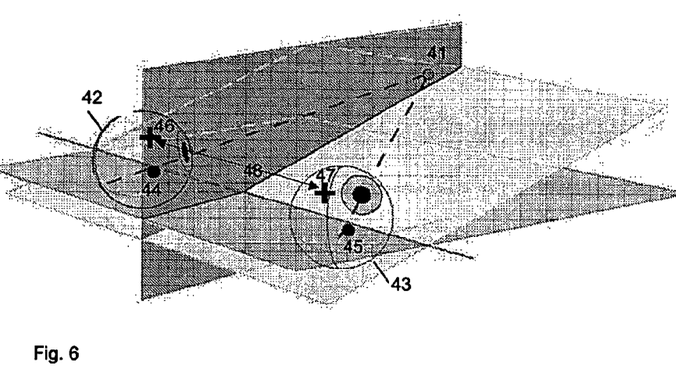

FIG. 6 shows an embodiment of the data acquisition method according to the invention, which is used to determine the distance 48 between a fixed-eyeball point 46 on the left eyeball 42, and a fixed-eyeball point 47 on the right eyeball 43. The connecting lines between the fixation point 41 and the mechanical oculogyric points 44 and 45 are defined as the lines of fixation. The fixed-eyeball points 46 and 47 must have an axial distance from the corresponding mechanical oculogyric point in the direction of each line of fixation. Since the fixed-eyeball points preferably do not lie in the light path, there is also a radial distance from the line of fixation.

Figure 7:
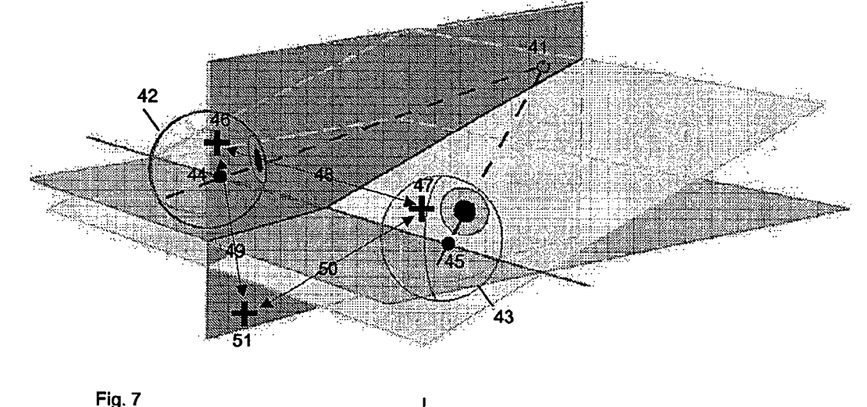

FIG. 7 shows an embodiment of the data acquisition method according to the invention, in which not only the distance 48 described in FIG. 6, but also the distances 49 and 50 are determined. The distances 49 and 50 represent the distances between the fixed-eyeball points 46 and 47 on the one hand, and a fixed-head reference point 51, on the other hand.

Figure 8:
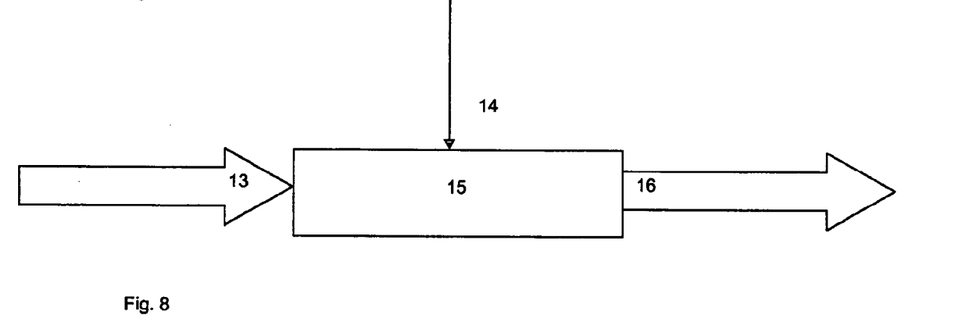

FIG. 8 shows a diagrammatic representation of the functions of the power supply system. The charging function 13 supplies power to the system. This can be accomplished e.g. with the aid of capacitive, inductive and electromagnetic waves. The body's physiological energy sources can also be used, such as for example the mechanical movement of muscles, blood or aqueous humour. The control signal 14 is passed into a storage and transformer unit 15. The electrical energy 16 is then discharged.

Figure 9:
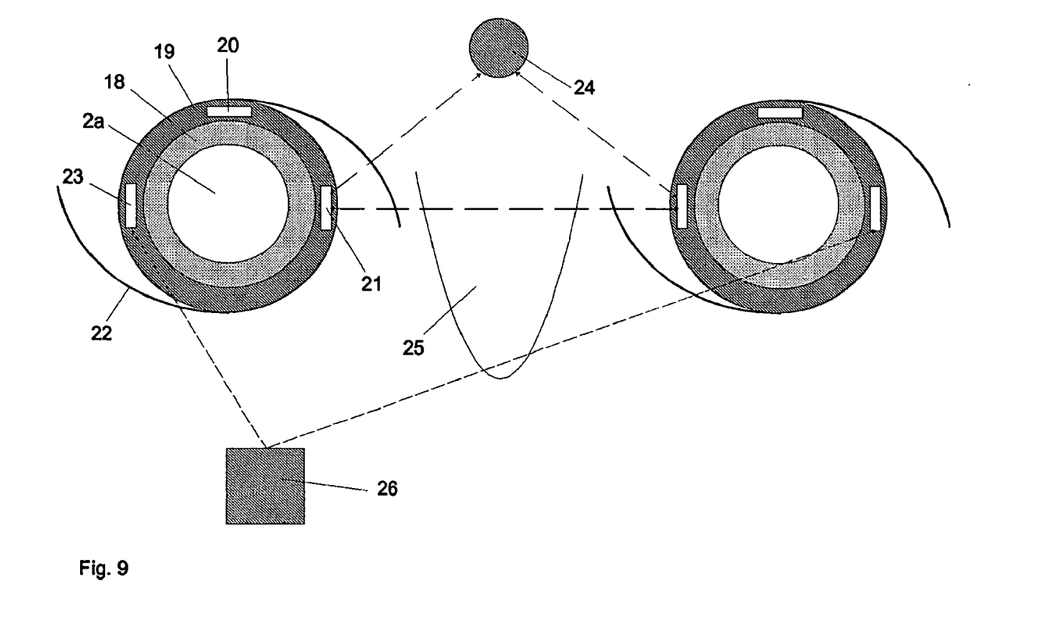

FIG. 9 shows an embodiment of the artificial accommodation system in front elevation, where an artificial accommodation system is implanted into each eye (binocular implantation).

Figure 10:
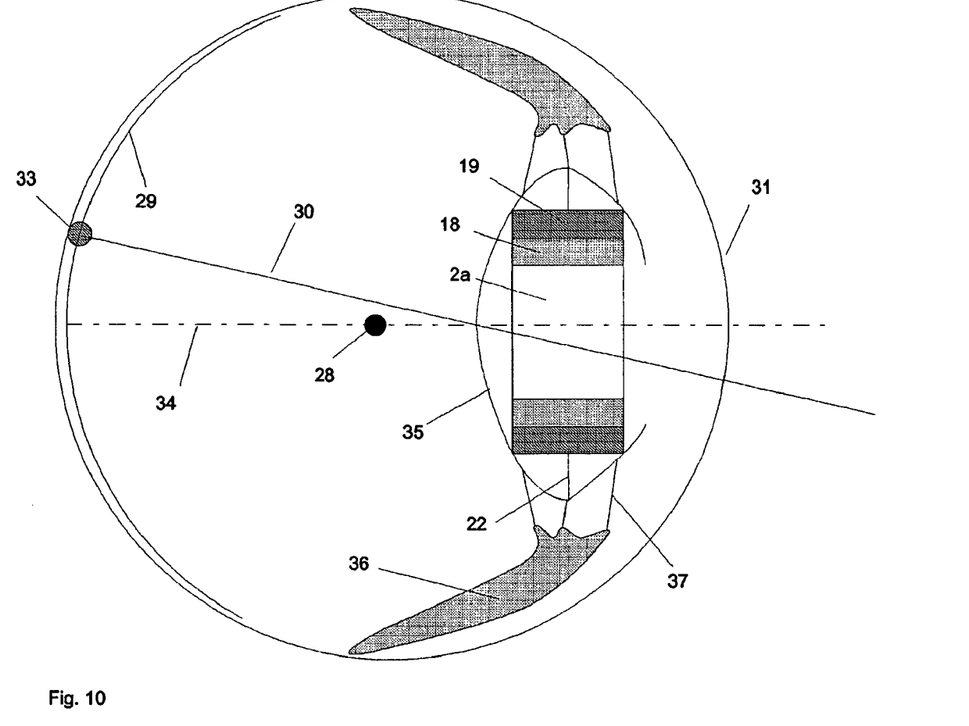

FIG. 10 shows an eye at a greater magnification, with an artificial accommodation system viewed from above.

The optical system, which is part of the dioptric apparatus, is an active optical element here. It is arranged in the light path behind the cornea 31 on the optical axis 34. It consists of an elastic lens 2a, with an actor 18 arranged around it in the form of a ring. The circumference of the construction space 19 accommodates the data processing system 20, part of the data acquisition system (fixed-eyeball point 21) and part of the power supply system 23 on the implant side. The fixed-head reference point, which can be used by both data systems, is denoted here by 24. It is arranged for example over the nose 25. The implant is fitted with elements for attachment 22. Another part of the power supply system 26 can be placed outside the body and it can transmit power to the part 23 on the implant side.

There is a mechanical oculogyric point 28 in the optical axis 34. The central groove (fovea centralis) 33 is at the intersection of the line of fixation 30 and the retina 29. The capsular sac 35 is surrounded by the ciliary body with the ciliary muscle 36 and the zonular fibres 37. The implant is fixed in the capsular sac 35 with the aid of elements of attachment 22.

Figure 11:
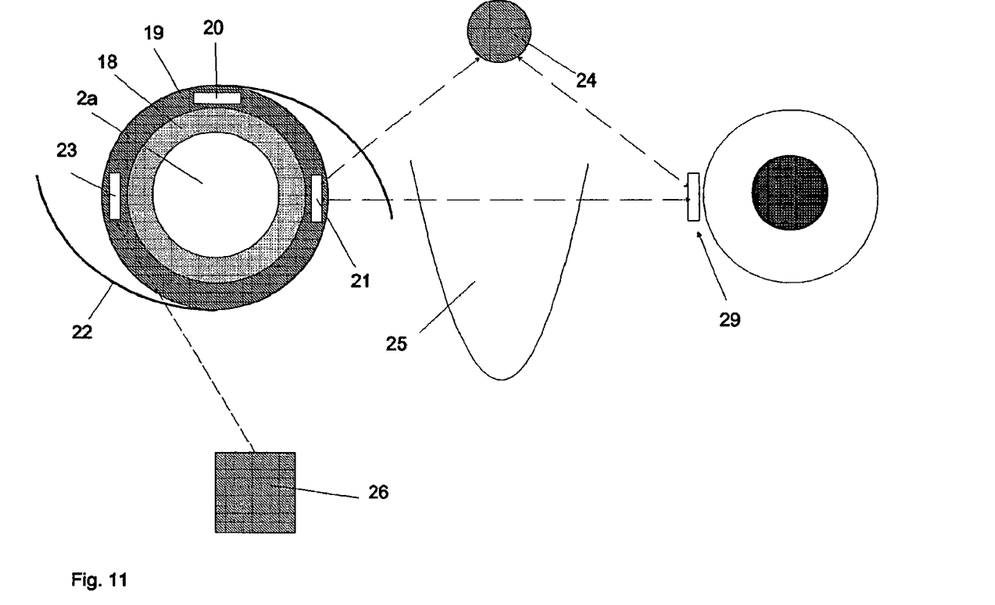

FIG. 11 shows an embodiment of the artificial accommodation system in front elevation, where an artificial accommodation system is implanted in the right eye (monocular implantation), and an auxiliary implant is placed on the outside of the eyeball of the other eye, where the auxiliary implant comprises at least one data acquisition system. Item 29 is the fixed-eyeball reference point on the eye without an implant, and specifically on the outer surface of the eyeball.

The invention claimed is:

1. An optical device for restoring the accommodative capacity of the eye, which comprises: a) at least one optical system b) at least one data acquisition system that does not touch the ciliary muscle and which has a means for detecting the spatial orientation of the two eyeballs with respect to each other, or it has means for measuring the diameter of the pupil and the luminance at least in one eye as a physiological control signal for accommodation c) at least one data processing system to produce a regulating signal for the optical system from the physiological characteristics received d) at least one power supply system, and e) at least one system for attachment, wherein an optical system, a data acquisition system, a data processing system, a power supply system and a system for attachment are combined to form an implant insertable into the capsular sac of an eye.

2. An optical device according to claim 1, wherein the optical system (3) is an active optical element with a variable curvature of a light refracting interface or a variable refractive index distribution, a displaceable passive optical element with invariable optical characteristics, or a combination of one or more active and/or passive optical elements.

3. An optical device according to claim 2, wherein the active optical element (3) comprises an electro-optical material, a compressible or incompressible fluid, an elastic solid body (2a), a wetting-angle system or a smart material (18) that generates internal forces due to its atomic and molecular structure.

4. An optical device according to claim 1, wherein the data acquisition system (8) comprises a distance-measuring apparatus operating by an acoustic, electromagnetic, optical or tactile process.

5. An optical device according to claim 1, wherein the data acquisition system (8) comprises an apparatus designed for detecting mechanical tension.

6. An optical device according to claim 1, wherein the need for accommodation can be obtained from the control signal of the diameter of the pupil and the absolute luminance in the light path, using the connection between accommodation and the pupillary near reflex.

7. An optical device according to claim 6, wherein the control signal of the diameter of the pupil can be obtained by a sensor designed to detect the movement of the iris muscle (71), and the luminance can be determined by a photodiode (74) designed to measure the brightness.

8. An optical device according to claim 1, wherein the need for accommodation can be obtained from the control signal of the motor activity of both eyes, via the connection between accommodation and oculomotor activity.

9. An optical device according to claim 8, wherein two mutually communicating data acquisition systems (21, 29) detect the control signal of the oculomotor activity by the contact-free determination of the distance between one or more points (46, 47) in or on the two eyes.

10. An optical device according to claim 9, wherein a fixed-head point (24, 51) is chosen whose distance from the points (46, 47) in or on the eyeballs can be determined by the data acquisition systems (21, 29) without contact.

11. An optical device according to claim 8, wherein two mutually communicating data acquisition systems detect the physiological control signal of the oculomotor activity by determining the angles of yaw of both eyes with respect to the head.

12. An optical device according to claim 1, wherein the data acquisition system takes the change in the shape of the ciliary sulcus as the physiological control signal of accommodation.

13. An optical device according to claim 12, wherein the change in the shape of the ciliary sulcus is determined by measuring the surface compression with the aid of a body (11a) inserted into the ciliary sulcus.

14. An optical device according to claim 1, wherein the data acquisition system detects the physiological control signal of accommodation from the contraction of the ciliary muscle.

15. An optical device according to claim 14, wherein the contraction of the ciliary muscle is determined by contact-free distance measurement carried out with the aid of a sensor (11).

16. An optical device according to claim 1, wherein a means for influencing the displacement of the capsular sac (66) is provided, and the data acquisition system takes the displacement of the capsular sac as the physiological control signal of accommodation.

17. An optical device according to claim 16, wherein the means for influencing the displacement of the capsular sac comprises elastic or magnetic bodies.

18. An optical device according to claim 16, wherein the displacement of the capsular sac is determined by distance measurement (67).

19. An optical device according to claim 18, wherein it is the distance between a stationary point in the eye (65) and a point on the capsular sac (64) that is measured.

20. An optical device according to claim 1, wherein the data processing system has hierarchical regulating structures, central/decentral structures, systems operating with adaptive algorithms or systems operating with self-learning algorithms, or it has a combination of these structures or systems.

21. An optical device according to claim 1, wherein the power is supplied by an external system (26) that is connected to the power supply system (23) arranged in the implant.

22. An optical device according to claim 1, wherein the power supply system puts the accommodation system in a state of minimum energy consumption (stand-by state) when the threshold value of luminance in the light path is not reached.

23. An optical device according to claim 1, wherein the power supply system has an internal power supply.

24. An optical device according to claim 23, wherein the internal power supply operates by using both physiological resources and the energy of light or technical energy storage devices.

25. An optical device according to claim 24, wherein the power supply system comprises batteries as technical energy storage devices.

26. An optical device according to claim 24, wherein the power supply system comprises fuel cells for utilizing physiological resources.

27. An optical device according to claim 1, wherein the system for attachment (22) makes a radial and axial centering in the light path possible and prevents tilting in the light path.

28. An optical device according to claim 27, wherein the system for attachment comprises fixing elements for axial and radial centering in the light path.

29. Method including the step of implanting the device of claim 1 in the eye.

* * * * *